US00PP14770P2

(12) United States Plant Patent
Snoeijer

(10) Patent No.: US PP14,770 P2
(45) Date of Patent: May 11, 2004

(54) CLEMATIS PLANT NAMED 'FASCINATION'

(50) Latin Name: *Clematis×hybrida*
Varietal Denomination: Fascination

(75) Inventor: Wim Snoeijer, Gouda (NL)

(73) Assignee: Plant Haven, Inc., Santa Barbara, CA (US)

( * ) Notice: Subject to any disclaimer, the term of this patent is extended or adjusted under 35 U.S.C. 154(b) by 52 days.

(21) Appl. No.: 10/366,004

(22) Filed: Feb. 13, 2003

(51) Int. Cl.[7] ..... A01H 5/00
(52) U.S. Cl. ..... Plt./228
(58) Field of Search ..... Plt./228

(56) References Cited

PUBLICATIONS

GTITM UPOVROM Citation for 'Fascination' as per QZ PBR 011505; Oct. 29, 2001.*

* cited by examiner

*Primary Examiner*—Kent Bell

(57) ABSTRACT

A new cultivar of Clematis named 'Fascination' that is characterized by upright to semi-climbing habit, glossy violet flowers in summer, glossy flower buds, silver seed heads, and medium to dark-green foliage. In combination these traits set 'Fascination' apart from all other existing varieties of Clematis known to the inventor.

2 Drawing Sheets

Genus: Clematis.
Species: ×*hybrida*.
Denomination: Fascination.

BACKGROUND OF THE INVENTION

The present invention relates to a new and distinct cultivar of Clematis that is grown for use as an ornamental in the landscape. The new cultivar is known botanically as Clematis and will be referred to hereinafter by the cultivar name 'Fascination'.

'Fascination' resulted from a formal breeding program that was established by the inventor in 1992 in Boskoop, Holland. The purpose of the breeding program was to produce free-flowering *integrifolia* type plants that are easy to propagate and less susceptible to pests and disease.

The female parent plant is *Clematis integrifolia* 'Olgae' (unpatented) and the male parent plant is *Clematis fusca* (unpatented). 'Fascination' is a hybrid plant that resulted from the hybridization between the pollen parent *Clematis fusca* and the seed parent *Clematis integrifolia* 'Olgae'. The cross was conducted by the inventor in a cultivated area of Boskoop, Holland. 'Fascination' was selected by the inventor in 1996 based on the unique glossy flower buds, glossy flowers, elegant flower shape, number of flowers, habit, and silver seed heads.

'Fascination' is a free-flowering perennial that exhibits an upright to semi-climbing habit, glossy violet flowers, glossy flower buds, silver seed heads, and medium to dark green leaves. Propagation is accomplished using softwood cuttings. There is no close comparison plant known to the inventor. 'Fascination' is distinguishable from the female parent plant *Clematis integrifolia* 'Olgae' in habit, flower color and flower shape, leaf shape and number of flowers per flower stalk. 'Fascination' is distinguishable from the male parent plant in flowering, flower shape, flower color, flower texture, number of flowers per flower stalk, and color of seed heads.

The first asexual propagation was accomplished by the inventor in 1997 in a cultivated area of Boskoop, Holland. Asexual propagation of the new cultivar 'Fascination' by cuttings at the location previously stated has shown that the unique features of this new Clematis are stable and the plant reproduces true to type in successive generations of asexual propagation.

SUMMARY OF THE INVENTION

The following represent the distinguishing characteristics of the new Clematis cultivar 'Fascination'. In combination these traits set 'Fascination' apart from all other existing varieties of Clematis known to the inventor. 'Fascination' has not been tested under all possible conditions and phenotypic differences may be observed with variations in environmental, climatic, and cultural conditions, however, without any variance in genotype.

1. Clematis 'Fascination' exhibits glossy violet flowers.
2. Clematis 'Fascination' is floriferous.
3. Clematis 'Fascination' is readily propagated using softwood cuttings.
4. Clematis 'Fascination' exhibits an upright to semi-climbing habit.
5. Clematis 'Fascination' is a perennial exhibiting elegantly shaped flowers.
6. Clematis 'Fascination' exhibits medium to dark-green foliage.
7. Clematis 'Fascination' exhibits silver seed heads.
8. Clematis 'Fascination' exhibits glossy flower buds.

BRIEF DESCRIPTION OF THE DRAWINGS

The accompanying color drawings illustrate the overall appearance of the new Clematis variety 'Fascination' showing the colors as true as it is reasonably possible to obtain in colored reproductions of this type. Colors in the drawings may differ from the color values cited in the detailed botanical description, which accurately describes the actual colors of the new variety 'Fascination'.

The drawing on sheet 1 illustrates the leaves, stems, buds and flowers from a side perspective.

The drawing on sheet 2 is a close-up view of the flowers. All drawings are made using conventional techniques and although foliage colors may appear different from actual colors due to light reflectance, they are as accurate as possible by conventional photography.

BOTANICAL DESCRIPTION OF THE PLANT

The following is a detailed description of the Clematis cultivar named 'Fascination'. Data was collected in Boskoop, Holland from 2-year-old plants grown in 2-litre containers out-of-doors. Color determinations are in accordance with The 2001 Royal Horticultural Society Colour Chart except where general color terms of ordinary dictionary significance are used. The growing requirements are similar to the species.

Botanical classification: Clematis 'Fascination'.
Species: ×*hybrida*.
Common name: Vase vine.
Use: Ornamental.
Parentage: 'Fascination' is a hybrid plant that resulted from the hybridization of the following parent plants:
*Seed parent.*—*Clematis integrifolia* 'Olgae'.
*Pollen parent.*—*Clematis fusca*.
Type: Perennial.
Vigor: Low vigor.
Sexuality: Bisexual.
Habit: Upright to semi-climbing.
Height (at maturity): 140 cm. in height.
Width (at maturity): 70 cm. in width.
Hardiness: USDA Zone 6.
Propagation: Softwood cuttings.
Root system: Slightly fleshy.
Soil: All moist but well-drained soils.
Sunlight: Full sun to semi-shade.
Time to initiate rooting: 4–6 weeks are needed to produce roots on an initial cutting.
Temperature to initiate rooting: 20° to 25° Centigrade air temperature.
Crop time: 12 months are needed to produce a finished 1-litre container from a rooted cutting.
Seasonal interest: Violet flowers in summer.
Disease and pests: Susceptible to mildew.
Stem:
*Stem diameter.*—0.3 cm. in diameter.
*Stem length.*—1.5 meters in length.
*Surface.*—Glabrous.
*Lenticels.*—None present.
*Stem color.*—200D.
*Internode length.*—6–12 cm. between nodes.
*Branching habit.*—Basal shoots.
Foliage:
*Type.*—Deciduous.
*Leaf arrangement.*—Opposite.
*Leaf division.*—Compound pinnate.
*Number of leaflets* (*per leaf*).—Two leaflets in number.
*Leaflet attachment.*—Sessile.
*Leaflet dimensions.*—1–5 cm. in length and 0.8–3 cm. in width.
*Leaflet shape.*—Lanceolate.
*Leaflet base.*—Oblique.
*Leaflet apex.*—Acute.
*Leaflet venation.*—Palmate.
*Leaflet margin.*—Entire and lobed.
*Leaflet color* (*adaxial surface*).—137C.
*Leaflet color* (*abaxial surface*).—137D.
*Vein color* (*adaxial surface*).—l47D.
*Vein color* (*abaxial surface*).—147D.
*Leaflet surface* (*adaxial*).—Glabrous.
*Leaflet surface* (*abaxial*).—Pubescent.
*Leaf attachment.*—Leaf is attached by a rachis.
*Rachis dimensions.*—4 cm. in length and 0.10 cm. in width.
*Rachis color.*—137D.
*Rachis surface.*—Pubescent.
*Stipules.*—None.
*Leaf dimensions.*—l0 cm. in length and 9 cm. in width.
*Foliar fragrance.*—Similar in fragrance to crushed leaves of Ligustrum.
Flower:
*Blooming season.*—Summer.
*Inflorescence type.*—Dichasial cyme.
*Flower arrangement.*—Spiral.
*Color of peduncle.*—97A.
*Peduncle length.*—2–5 cm. in length.
*Peduncle width.*—0.15 cm. in width.
*Peduncle surface.*—Pubescent.
*Self-cleaning or persistent.*—Self-cleaning.
*Diameter of flower.*—3.5 cm. in diameter.
*Flower shape.*—Urceolate with campanulate apex.
*Aspect.*—Nodding.
*Petals.*—Apetalous.
*Tepals.*—Four tepals.
*Color of tepals* (*adaxial and abaxial surfaces*).—79B.
*Tepal shape.*—Elliptic.
*Tepal apex.*—Acute.
*Tepal base.*—Truncate.
*Tepal surface* (*adaxial surface*).—Glossy with small amount of short hairs.
*Tepal surface* (*abaxial surface*).—Glossy with small amount of short hairs.
*Tepal margin.*—Entire.
*Tepal margin color* (*abaxial surface*).—155B.
*Tepal margin color* (*Adaxial color*).—155B.
*Tepal length.*—1.8 cm. in length.
*Tepal width.*—1 cm. in width.
*Unfused or fused.*—Tepals are unfused.
*Bud color.*—Closest to 79A but darker.
*Bud shape.*—Ovate.
*Bud dimensions.*—1.5 cm. in length and 0.8 cm. in width.
*Quantity of flowers per branch.*—Approximately 50+ per branch.
*Lastingness of flower.*—An individual flower with last 10 days on the plant (from bud to tepals falling off) and 5–8 days off the plant.
*Fragrance.*—Slightly sweet.
Reproduction organs:
*Stamens.*—+50.
*Color of stamens.*—156D
*Dimensions of stamen.*—0.4–0.9 cm. in length and 0.1 cm. in width.
*Dimensions of anther.*—10 mm. in width and 40 mm. in length.
*Pollen color.*—10D.
*Amount of pollen.*—Large amount.
*Anther color.*—10D.

*Anther shape.*—Filiform.
*Pistils.*—+25.
*Pistil shape.*—Plumose.
*Pistil color.*—155A.
*Stigma color.*—155A.
*Ovary position.*—Superior.
*Ovary color.*—Green.

Seed:

*Number of seeds.*—+20.
*Seed shape.*—Orbicular.
*Seed color.*—First green, then turning dark brown.
*Seed dimensions.*—0.5 cm. in length and 0.6 cm. in width.

I claim:

1. A new and distinct variety of Clematis plant named 'Fascination' as described and illustrated.

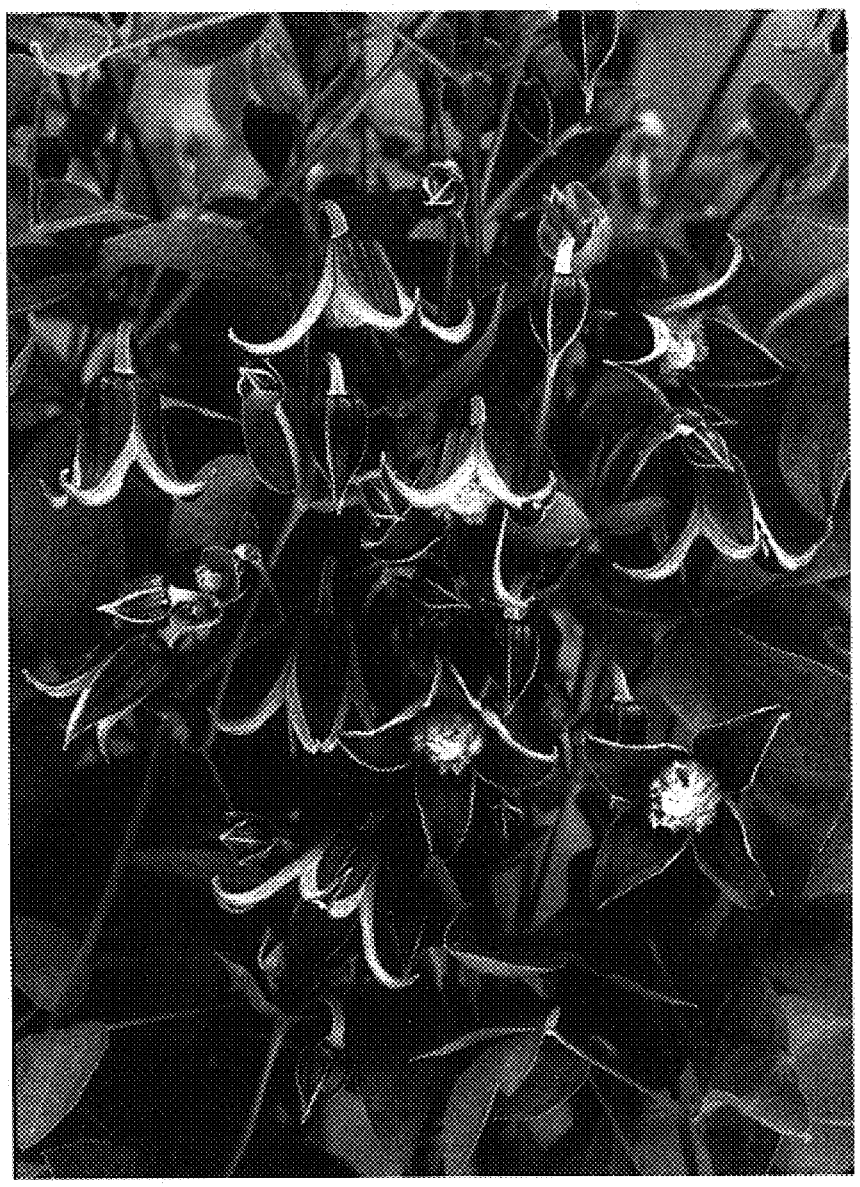

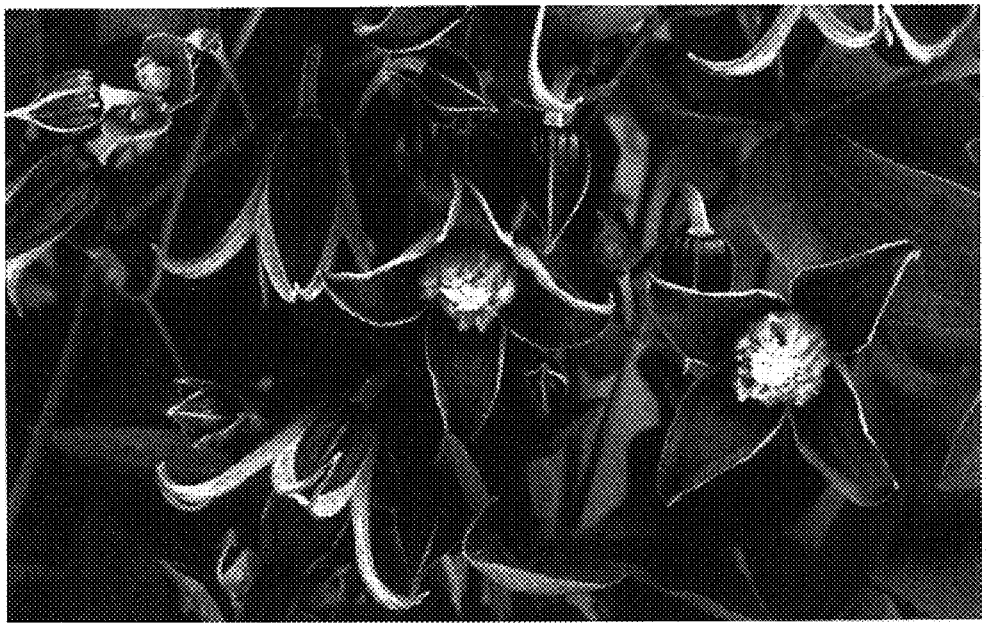

* * * * *